US006774180B2

(12) United States Patent
Kozlowski et al.

(10) Patent No.: US 6,774,180 B2
(45) Date of Patent: Aug. 10, 2004

(54) SYNTHESIS OF HIGH MOLECULAR WEIGHT NON-PEPTIDIC POLYMER DERIVATIVES

(75) Inventors: Antoni Kozlowski, Huntsville, AL (US); Xiaoming Shen, Madison, AL (US); Michael David Bentley, Huntsville, AL (US); Zhihao Fang, Madison, AL (US)

(73) Assignee: Nektar Therapeutics AL, Corporation, Huntsville, AL (US)

( * ) Notice: Subject to any disclaimer, the term of this patent is extended or adjusted under 35 U.S.C. 154(b) by 225 days.

(21) Appl. No.: 10/024,357

(22) Filed: Dec. 18, 2001

(65) Prior Publication Data

US 2002/0082345 A1 Jun. 27, 2002

Related U.S. Application Data

(60) Provisional application No. 60/256,801, filed on Dec. 18, 2000.

(51) Int. Cl.[7] ........................ C08G 63/50; C08G 63/91; A61K 38/00
(52) U.S. Cl. ..................... 525/54.1; 525/54.2; 525/398; 525/399; 525/400; 525/437; 525/535; 525/539; 525/540; 514/2; 514/23; 514/44; 514/54; 514/103; 514/476; 514/506; 514/553; 514/580
(58) Field of Search ............................. 525/54.1, 54.2, 525/398, 399, 400, 437, 535, 539, 540; 514/2, 23, 44, 54, 103, 476, 506, 553, 580

(56) References Cited

U.S. PATENT DOCUMENTS

| | | | |
|---|---|---|---|
| 4,670,417 A | 6/1987 | Iwasaki et al. | |
| 5,252,714 A | 10/1993 | Harris et al. | |
| 5,281,698 A | 1/1994 | Nitecki | |
| 5,468,478 A | 11/1995 | Saifer et al. | |
| 5,650,234 A | 7/1997 | Dolence et al. | |
| 5,672,662 A | 9/1997 | Harris et al. | |
| 5,824,784 A | 10/1998 | Kinstler et al. | |
| 5,900,461 A | 5/1999 | Harris | |
| 5,932,462 A | 8/1999 | Harris et al. | |
| 6,348,558 B1 | 2/2002 | Harris et al. | |

FOREIGN PATENT DOCUMENTS

| WO | WO 99/45964 A1 | 9/1999 |
|---|---|---|
| WO | WO 01/26692 A1 | 4/2001 |

OTHER PUBLICATIONS

Samuel Zalipsky, "Chemistry of polyethylene glycol conjugates with biologically active molecules", *Advanced Drug Delivery Reviews*, vol. 16, pp. 157–182 (1995).
Okamoto et al., "Kinetic Study on Reactions Between Polymer Chain–Ends—II. Reactions Between Chlorosulphonyl–Ended and Primary Amino–Ended Polyoxyethylenes Followed by Fluorometry", *Eur. Polym. J.*, vol. 19, No. 4, pp. 341–346 (1983).

Greenwald et al., "Highly Water Soluble Taxol Derivatives: 7–Polyethylene Glycol Carbamates and Carbonates," *J. Org. Chem.*, 60, pp. 331–336 (1995).
Buckman et al., "Functionalization of Poly(ethylene glycol) and Monomethoxy–Poly(ethylene glycol)," *Makromol. Chem.*, 182, pp. 1379–1384 (1981).
Zalipsky et al., "Attachment of Drugs to Polyethylene Glycols," *Eur. Polym. J.*, vol. 19, No. 12, pp. 1177–1183 (1983).
Andresz et al., *Makromol. Chem.*, 179, pp. 301–312 (1978).
Olson et al., "Preparation and Characterization of Poly(ethylene glycol)ylated Human Growth Hormone Antagonist," *Chemistry & Biological Applications*, pp. 170–181 (1997).
Abuchowski et al., "Cancer Therapy with Chemically Modified Enzymes. I. Antitumor Properties of Polyethylene Glycol–Asparaginase Conjugates," *Cancer Biochem. Biophys*, vol. 7, pp. 175–186 (1984).
Joppich et al., "Synthesis of Glycyl–L–tryptophylglycine Substituted by Poly(ethylene oxide) at both the Carboxy and the Amino End Groups," *Makromol. Chem.*, 180, pp. 1381–1384 (1979).
Pitha et al., "Detergents Linked to Polysaccharides: Preparation and Effects on Membranes and Cells," *Eur. J. Biochem.*, 94, pp. 11–18 (1979).
Elling et al., "Immunoaffinity Partitioning: Synthesis and Use of Polyethylene Glycol–Oxirane for Coupling to Bovine Serum Albumin and Monoclonal Antibodies," *Biotechnology and Applied Biochemistry*, 13, pp. 354–362 (1991).
Beauchamp et al., "A New Procedure for Synthesis of Polyethylene Glycol–Protein Adducts; Effects on Function, Receptor Recognition, and Clearance of Superoxide Dismutase, Lactoferrin, and $\alpha_2$–Macroglobulin," *Analytical Biochemistry*, 131, pp. 25–33 (1983).
Tondelli et al., "Poly(Ethylene Glycol) Imidazolyl Formates as Oligomeric Drug–Binding Matrices," *Journal of Controlled Release*, 1, pp. 251–257 (1985).
Veronese et al., "Activation of Monomethoxy–Polyethylene Glycols by Phenylchloroformates and Modification of Ribonuclease and Superoxide Dismutase," *Applied Biochemistry and Biotechnology*, vol. 11, pp. 141–152 (1985).
Sartore et al., "Enzyme Modification by MPEG with an Amino Acid or Peptide as Spacer Arms," *Applied Biochemisty and Biotechnology*, vol. 27, pp. 45–54 (1991).
Harris et al., "Synthesis and Characterization of Poly(ethylene glycol) Derivatives," *J. Polym. Sci. Chem. Ed.*, vol. 22, pp. 341–352 (1984).

(List continued on next page.)

*Primary Examiner*—Samuel A. Acquah
(74) *Attorney, Agent, or Firm*—Alston & Bird LLP

(57) ABSTRACT

High molecular weight derivatives of activated poly (ethylene glycol) and the like polymers are prepared in high purity by conjugating a large PEG molecule to a small PEG molecule. Most of the reaction steps can be accomplished on the more readily purified small molecule to avoid laborious purification of the high molecular weight derivatives.

45 Claims, No Drawings

OTHER PUBLICATIONS

Goodson et al., "Site–Directed PEGylation of Recombinant Interleukin–2 at its Glycosylation Site," *Bio/Technology,* vol. 8, No. 4, pp. 343–346, (1990).

Romani et al., "Synthesis of Unsymmetrical Cystine Peptides: Directed Disulfide Pairing with the Sulfenohydrazide Method," *Chemistry of Peptides and Proteins,* vol. 2, pp. 29–34 (1984).

Kogan, "The Synthesis of Substituted Methoxy–Poly(ethylene glycol) Derivatives Suitable for Selective Protein Modification," *Synthetic Communications,* 22(16), pp. 2417–2424 (1992).

Woghiren et al., "Protected Thiol–Polyethylene Glycol: A New Activated Polymer for Reversible Protein Modification," *Bioconjugate Chem.,* 4, pp. 314–318 (1993).

Sawhney et al., "Bioerodible Hydrogels Based on Photopolymerized Poly(ethylen glycol)–co–poly($\alpha$–hydroxy acid) Diacrylate Macromers," *Macromolecules,* 26, pp. 581–587 (1993).

SYNTHESIS OF HIGH MOLECULAR WEIGHT NON-PEPTIDIC POLYMER DERIVATIVES

CROSS-REFERENCE TO RELATED APPLICATIONS

This application claims the benefit of Provisional Application Serial No. 60/256,801, filed Dec. 18, 2000, which is incorporated herein by reference in its entirety.

FIELD OF THE INVENTION

The invention relates to derivatives of poly(ethylene glycol) and related polymers and methods for their synthesis. More particularly, the invention relates to high molecular weight derivatives and methods of producing high molecular weight derivatives.

BACKGROUND OF THE INVENTION

Covalent attachment of the hydrophilic polymer poly(ethylene glycol), abbreviated PEG, also known as poly(ethylene oxide), abbreviated PEO, to molecules and surfaces is of considerable utility in biotechnology and medicine. In its most common form, PEG is a linear polymer terminated at each end with hydroxyl groups:

$$HO-CH_2CH_2O-(CH_2CH_2O)_n-CH_2CH_2-OH$$

The above polymer, α, ω-dihydroxypoly(ethylene glycol), can be represented in brief form as HO-PEG-OH where it is understood that the -PEG- symbol represents the following structural unit:

$$-CH_2CH_2O-(CH_2CH_2O)_n-CH_2CH_2-$$

where n typically ranges from about 3 to about 4000.

PEG is commonly used as methoxy-PEG-OH, or mPEG in brief, in which one terminus is the relatively inert methoxy group, while the other terminus is a hydroxyl group that is subject to ready chemical modification. The structure of mPEG is given below.

$$CH_3O-(CH_2CH_2O)_n-CH_2CH_2-OH$$

The copolymers of ethylene oxide and propylene oxide are closely related to PEG in their chemistry, and they can be substituted for PEG in many of its applications.

$$HO-CH_2CHRO(CH_2CHRO)_nCH_2CH_2-OH$$

where R=H or alkyl, such as $CH_3$.

PEG is also commonly used in multi-arm forms in which linear PEGs are attached to a central core:

$$R(-O\text{-}PEG\text{-}OH)_n$$

where R is a core derived from, for example, pentaerythritol or glycerol oligomers. PEGs can also be prepared with degradable linkages in the backbone.

PEG is a polymer having the properties of solubility in water and in many organic solvents, lack of toxicity, and lack of immunogenicity. One use of PEG is to covalently attach the polymer to insoluble molecules to make the resulting PEG-molecule "conjugate" soluble. For example, it has been shown that the water-insoluble drug paclitaxel, when coupled to PEG, becomes water-soluble. Greenwald, et al., *J. Org. Chem.*, 60:331–336 (1995).

To couple PEG to a molecule, such as a protein, it is often necessary to "activate" the PEG to prepare a derivative of the PEG having a functional group at the terminus. The functional group can react with certain moieties on the protein, such as an amino group, thus forming a PEG-protein conjugate. Many activated derivatives of PEG have been described. An example of such an activated derivative is the succinimidyl succinate "active ester":

$$CH_3O\text{-}PEG\text{-}O_2C\text{-}CH_2CH_2\text{-}CO_2\text{-}NS$$

where NS=

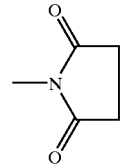

Hereinafter, the succinimidyl active ester moiety will be represented as $-CO_2-NS$. Such activated PEGs can also be prepared from the above described multi-arm forms or from branch forms such as:

$$(PEG\text{-}O\text{-}CO-NH)_2LYS\text{-}NS$$

as described in Harris, et al., U.S. Pat. No. 5,932,462, which is incorporated by reference herein in its entirety. Functional groups can be attached to the terminus of PEG by direct conversion of the starting hydroxyl to other forms or by attachment of organic spacer groups to the hydroxyl group. For example, the succinate PEG above is prepared by attachment of succinic anhydride to PEG. Similarly one can react glutaric anhydride to prepare PEG glutarate, $PEG\text{-}O_2C\text{-}CH_2CH_2CH_2\text{-}CO_2H$. Even larger aliphatic spacers can be added. As described in Okamoto, et al., *Eur. Polym. J.*, 19, 341–346 (1983), PEG can be converted to a PEG amine by reacting PEG-OH with $ONC-(CH_2)_6-NCO$ and then converting the remaining isocyanate to amine product $PEG\text{-}O_2CNH-(CH_2)_6-NH_2$.

As applications of PEG chemistry have become more sophisticated, there has been an increasing need for high molecular weight, high purity PEG derivatives. The synthesis of these compounds is complicated by the difficulty in removing polymeric impurities that accumulate during multi-step preparations. Small molecule impurities are normally easily removed by simple procedures such as precipitation. However, high molecular weight polymeric side-products are generally quite difficult to remove and require utilization of time-consuming and expensive chromatographic techniques. There remains a need in the art for improved methods of preparing high molecular weight PEG derivatives.

SUMMARY OF THE INVENTION

The invention includes high molecular weight activated polymer derivatives and methods for making them. A small, difunctional oligo(ethylene glycol) ("OEG") derivative or similar oligomer or small polymer is covalently linked to a large poly(ethylene glycol) polymer ("PEG") derivative or similar polymer. In this way, most of the chemical transformations can be conducted on the oligomeric or small polymeric compound. Large polymeric impurities are more difficult to separate from the desired product than are smaller ones, and the products of these reactions involving these polymers typically include unreacted reagents, difunctional components that can result in cross linking, partially reacted components, and other polymeric impurities. The invention avoids these impurities by reducing the number of reactions needed to create the large polymer.

Thus, as shown below, one can make a complicated polymeric compound in one step by reacting a complicated oligomer, for example, Y'—OEG-Y, where Y and Y' are active moieties, with a simple high molecular weight polymeric compound, for example, mPEG-Z, where Z reacts with one of Y or Y', to make a new linking group X between the larger PEG and the smaller PEG. In this way, polymeric impurities do not accumulate. Y and Y' can be the same or different, but should be chosen so that the two moieties are compatible and will not react with each other.

In a typical reaction for producing a high molecular weight monofunctional large molecule, a monomethoxy poly(ethylene glycol) is reacted with a smaller PEG polymer, in which the functional group Z on the monofunctional larger PEG polymer reacts with the functional group Y' on the heterobifunctional smaller polymer. The high molecular weight product retains the active group Y. The reactants are linked by a group X formed by the reaction of the Z and Y' moieties. This reaction can be illustrated as follows:

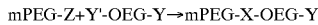

For example, an mPEG-propionic acid of molecular weight 32,000 which is a compound typically made in several steps from mPEG-OH, can be prepared in a single step by reacting an activated MPEG carbonate 30,000 that has been prepared in one step from mPEG-OH, with α-amino-ω-propionic acid of molecular weight 2000. Most of the chemical transformations can be performed on the small, inexpensive, more readily purified PEG 2000.

Monofunctional, homobifunctional, and heterobifunctional large molecules can be prepared by the practice of the invention, although not necessarily all with equivalent results. Reactions that tend to introduce complications in the larger polymeric component of the product molecule may reduce the effectiveness of the method if impurities are increased with multiple reaction steps.

In a somewhat more generalized embodiment, showing a poly(ethylene glycol) polymer with greater specificity, the structure of the products of the invention can be described as follows:

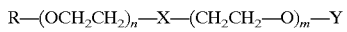

The above structure is prepared by reacting R—(OCH$_2$CH$_2$)$_n$—Z with Y'—(CH$_2$CH$_2$—O)$_m$—Y, where Z is a group reactive with Y' and neither Y nor R is reactive with Z or Y'. R can be a capping moiety, including various alkyl moieties, typically methoxy as attached to PEG. R can also be a reactive group or a protected reactive group Y" in which the reactive group can be deprotected and available for reaction at some later desired time. Y and Y' can be the same if Y' has been a protected group or a different group that does not participate in the reactions used to create the product molecule. Functional groups include, but are not limited to, aldehyde, maleimide, active ester, thiosulfonate or amine. X is a small, hydrophilic linker such as amide or carbamate; n is from about 200 to 2000; and m is from about 1 to 120. X is desirably a small and hydrophilic moiety that will not adversely impact the chemical and physical properties of the resulting high molecular weight polymer.

Alternatively, a large polymeric segment that is bifunctional or has additional functionality can be linked to smaller molecules at one or more functionalities. The functionality of the product large molecule can originate from the large polymeric segment or the smaller oligomeric or polymeric segment, as desired. The polymer backbone can have groups or linkers subject to hydrolysis or enzymatic degradation built into the backbone if desired for controlled degradability of the product molecule.

The polymer segments above may broadly be thought of as (Poly)$_a$ for the larger polymer segment and (Poly)$_b$ for the smaller polymer segment where poly can be any of the polymers including poly(ethylene glycol) in its various forms and polymers considered in the art to be of similar characteristics.

Thus, a high molecular weight polymer can be prepared from a lower molecular weight polymer, from which it is much less troublesome to remove impurities, and a higher molecular weight polymer that has not been subjected to a series of reactions or complex purification steps to remove polymeric impurities.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

Definitions

The terms "functional group," "active moiety," "activating group," "reactive site," "endgroup," "chemically reactive group," and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with functional groups, is intended to include those functional groups that react readily with electrophilic or nucleophilic groups on other molecules, in contrast to those groups that require strong catalysts or highly impractical reaction conditions to react (i.e., "non-reactive" or "inert" groups). For example, as would be understood in the art, the term "active ester" would include those esters that react readily with nucleophilic groups such as amines. Exemplary active esters include N-hydroxysuccinimidyl esters or 1-benzotriazolyl esters. Typically, an active ester will react with an amine in aqueous medium in a matter of minutes, whereas certain esters, such as methyl or ethyl esters, require a strong catalyst in order to react with a nucleophilic group.

The term "alkyl" refers to hydrocarbon chains typically ranging from about 1 to about 12 carbon atoms in length, and includes straight and branched chains. The hydrocarbon chains may be saturated or unsaturated. The term "substituted alkyl" refers to an alkyl group substituted with one or more non-interfering substituents, such as, but not limited to, C$_3$–C$_6$ cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like.

As used herein, "non-peptidic" refers to a polymer backbone substantially free of peptide linkages. However, the polymer backbone may include a minor number of peptide linkages spaced along the length of the backbone, such as, for example, no more than about 1 peptide linkage per about 50 monomer units.

A "polymer conjugate" refers to a water soluble polymer backbone covalently attached to a biologically active molecule, as defined herein. In the case that a polymer conjugate is reacted with a second polymer so as to form an extended polymer backbone, whether or not the joinder of the polymers is with a peptidic or other linkage, the term "polymer conjugate" refers to the overall length of polymer bound to the biologically active agent.

The term "linkage", "linker", or "linking group" is used herein to refer to groups or bonds that normally are formed as the result of a chemical reaction and typically are covalent linkages. Hydrolytically stable linkages means that the linkages are substantially stable in water and do not react with water at useful pHs, e.g., under physiological conditions for an extended period of time, preferably indefinitely.

Hydrolytically unstable or degradable linkages means that the linkages are degradable in water or in aqueous solutions, including for example, blood. Enzymatically unstable or degradable linkages means that the linkage can be degraded by one or more enzymes.

The term "biologically active molecule", "biologically active moiety", "biologically active agent", or "drug" when used herein means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

The terms "low weight polymer" and "low molecular weight polymer" broadly refer to a linear, branched, multi-arm, or forked polymer backbones comprising a water-soluble and non-peptidic polymer having from 1 to about 120 repeating units. These polymers typically have from 1 to 2 functional groups, typically located at opposite termini on a linear polymer, to about 300, which can be located at the termini of highly branched or multiarmed structures, although a smaller number may be located along the polymer backbone. Suitable polymers include, but are not limited to poly(alkylene glycol), such as poly(ethylene glycol) (PEG), poly(propylene glycol) (PPG), copolymers of ethylene glycol and propylene glycol and the like, poly(oxyethylated polyol), poly(olefinic alcohol), poly(vinylpyrrolidone), poly(hydroxypropylmethacrylamide), poly(($\alpha$-hydroxy acid), poly(vinyl alcohol), polyphosphazene, polyoxazoline, and copolymers, terpolymers, derivatives and mixtures thereof. It should be understood that oligomeric and even monomeric lengths are to be included in the above. Although the molecular weight of the small polymer or oligomer can vary, it is typically in the range of from about 100 Da to about 10,000 Da, depending, of course, on the molecular weight of the individual repeating units. In the case of PEG, one PEG monomer unit has a molecular weight of about 44 Da and low weight polymers will have a molecular weight of from about 44 Da to about 5280 Da. Molecular weights of 2000, 3200, 3400, and 5,000 are commonly available commercially. Those of ordinary skill in the art will recognize that the foregoing list for substantially water soluble and non-peptidic polymer backbones is by no means exhaustive and is merely illustrative, and that all polymeric materials having the qualities described above are contemplated.

The terms "high weight polymer" and "high molecular weight polymer" broadly refer to a linear, branched, or multi-arm polymer backbone comprising a water-soluble and non-peptidic polymer having more than about 200 repeating units. These polymers typically have from 1 to 2 functional groups, typically located at opposite termini on a linear polymer, to about 300, which can be located along the polymer backbone or at the termini of highly branched or multiarmed structures. Forked structures are also contemplated in which a terminus is branched to provide two functionalities. Suitable polymers include, but are not limited to these same polymers from which the low weight polymer is selected. Although the molecular weight of the polymer can vary, it is typically greater than about 8,000 Da depending, of course, on the molecular weight of the individual monomer units. In the case of PEG, high weight polymers have a molecular weight above about 8,800 Da. Commercially available PEGs include those having a nominal molecular weight of 10,000, 12,000, 15,000, 18,000, and 20,000, 30,000, 40,000 and above. Branched PEGs are readily available at higher molecular weights. Those of ordinary skill in the art will recognize that the foregoing list for substantially water soluble and non-peptidic polymer backbone is by no means exhaustive and is merely illustrative, and that all polymeric materials having the qualities described above are contemplated.

As used herein, "PEG" broadly refers to a linear, multi-arm, or branched polymer backbone comprising a water-soluble and non-peptidic polymer having repeat $CH_2CH_2O$ units. The polymer $\alpha$, $\omega$-dihydroxypoly(ethylene glycol), can be represented in brief form as HO-PEG-OH where it is understood that the -PEG- symbol represents the following structural unit —$CH_2CH_2O$—$(CH_2CH_2O)_n$—$CH_2CH_2$— where n typically ranges from about 3 to about 2000. The PEG family of polymers generally exhibits the properties of solubility in water and in many organic solvents, lack of toxicity, and lack of immunogenicity. The term PEG should be understood to be inclusive and to include poly(ethylene glycol) in any of its linear, branched or multi-arm forms, including alkoxy PEG, bifunctional PEG, forked PEG, branched PEG, pendant PEG, or PEG with degradable linkages therein.

PEG, in any of the forms described herein, is typically clear, colorless, odorless, soluble in water, stable to heat, inert to many chemical agents, does not hydrolyze or deteriorate (unless specifically designed to do so), and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects.

Random or block copolymers of ethylene oxide and propylene oxide, shown of either the high weight or low weight polymers of the invention wherein -PEG- is replaced with:

and wherein each R is independently H or $CH_3$, and c is as described above for m and n, depending on whether the molecule is a small or large one.

The term "polymer derivative" is sometimes used to describe the high weight polymer product of the invention having a high weight polymer segment and a low weight polymer segment joined by a linkage. The term is merely one of convenience, and is used to differentiate the product polymer from its high weight and low weight polymer components when so indicated.

In one form useful in the invention, the high molecular weight polymer is linear PEG terminated at one end with a hydroxyl group and the other end with a functional group, Z:

$$HO-CH_2CH_2O-(CH_2CH_2O)_n-CH_2CH_2-Z$$

The above polymer can be represented in brief form as HO-PEG-Z where it is understood that the -PEG- symbol represents the following structural unit:

$$-CH_2CH_2O-(CH_2CH_2O)_n-CH_2CH_2-$$

where n is greater than 200, and typically ranges from about 200 to 2000 for the high weight polymer. This polymer can also be represented more generically as $R-(Poly)_a-Z$, where $(Poly)_a$ stands for the large polymer component of the invention and R is a capping moiety or a suitable reactive group or protected reactive group Y".

Another type of PEG useful as the high weight polymer of the invention, $(Poly)_a$ is methoxy-PEG-Z, or mPEG-Z in brief, in which one terminus is the relatively inert methoxy group, while the other terminus is the functional group, Z. The structure of MPEG is given by:

$$CH_3O-(CH_2CH_2O)_n-CH_2CH_2-Z$$

where n is as described above. The use of an mPEG having a functional group, Z, or having other active sites of the polymer than Z capped by alkyl, aryl, or other non-reactive groups or protective groups prevents the high weight polymer from self-polymerizing and from undesirably combining with other molecules in the reaction mixture.

The functional group, Z, of the high weight polymer is selected such that the Z group readily forms a covalent bond with a corresponding reactive species, Y or Y', found on the low weight polymer thereby forming a linkage, X, between the high weight polymer and low weight polymer when reacted. Suitable functional groups are discussed below.

As an exemplary form useful in the practice of the invention, the low molecular weight polymer is a linear PEG polymer terminated at one end with a functional group, Y or Y', capable of readily forming a hydrolytically stable linking group when reacted with the Z component of the high weight polymer, and an additional functional group, Y or Y', capable of forming a covalent bond with a biologically active agent or of being modified to a form which is capable of forming a covalent bond with a biologically active agent:

$$Y'-CH_2CH_2O-(CH_2CH_2O)_m-CH_2CH_2-Y$$

The above polymer can be represented in brief form as Y'-PEG-Y where it is understood that the -PEG- symbol represents the following structural unit:

$$-CH_2CH_2O-(CH_2CH_2O)_m-CH_2CH_2-$$

where m ranges from 1 to about 120, and is typically less than about 60, for the low weight polymer. More generically, the polymer can be represented as $Y'-(Poly)_b-Y$, where $(Poly)_b$ stands for the small polymer component of the invention. The functional groups Y' and Y of the low weight polymer are selected so that they do not readily bond with each other under reaction conditions, thus avoiding self-polymerization of the low weight polymer. Acceptable Y' and Y groups are specified more fully below. below, are closely related to PEG in their chemistry, and can also be used as the polymer backbone The polymer backbones may also comprise a branched structure, typically having a central branching core moiety and a plurality of polymer chains, preferably linear polymer chains, linked to the central core. In one embodiment, PEG is used in a branched form prepared, for example, by addition of ethylene oxide to various polyol central core structures, such as glycerol, glycerol oligomers, pentaerythritol and sorbitol. Any polyol providing a plurality of hydroxyl groups available for conjugation to polymer chains may be used in the practice of the invention. The polyol branching core structure can provide from about 3 to 100 available hydroxy groups, and typically provides about 3 to 20, so that the branched polymer structure has from about 3 to 100 polymer chains. The branched poly(ethylene glycol) molecules of this type can be represented in general form as $R(-PEG-OH)_a$ in which R is derived from a central core moiety, such as glycerol, glycerol oligomers, or pentaerythritol, and "a" represents the number of arms, typically about 3 to 20.

For use as the high molecular weight polymer, the hydroxyl groups of the branched PEG normally are converted to functional groups Z prior to combination with the low weight polymer. Branched or multi-armed high weight polymers have the form $R(-PEG-Z)_a$, and are capable of bonding to about 3 to 20 of the low weight polymers of the invention, depending on the degree of branching or the number of arms having active groups. The central core moiety of the branched molecule can be derived from any of a number of amino acids, such as lysine, wherein the central core moiety typically provides two or more sites, e.g., amino groups, for attachment of polymer chains. Multi-armed PEG molecules, such as those described in U.S. Pat. No. 5,932, 462, which is incorporated by reference herein in its entirety, can also be used as the polymer backbone.

The polymer backbone of the high molecular weight polymer may alternatively comprise a forked PEG. An example of a forked PEG is represented by $PEG-ACHZ_2$, where A is a linking group and Z is an activated terminal group linked to CH by a chain of atoms of defined length. International Application No. PCT/US99/05333, the contents of which are incorporated by reference herein, discloses various forked PEG structures for use in one embodiment of the invention. The chain of atoms linking the Z functional groups to the branching carbon atom serve as a tethering group and may comprise, for example, alkyl chains, ether chains, ester chains, amide chains and combinations thereof. The Z functional groups can be used in the present invention to react with one of the functional groups, Y or Y', on the low weight polymer to form a linkage between the low weight and the high weight polymers.

The polymer backbone of either the low or high weight polymer may comprise a pendant PEG molecule having functional groups, Z, Y, or Y' as the case may be, covalently attached along the length of the PEG backbone rather than at the end of the PEG chain. The pendant reactive groups can be attached to the PEG backbone directly or through a linking moiety, such as alkylene.

In the case of a high weight polymer having more than one functional group, Z, there are many sites along the polymer where the corresponding functional group, Y or Y', on the low weight polymer may bond. The polymer derivatives produced therefrom are represented for convenience as:

$$PEG\text{-}[X\text{---}(CH_2CH_2O)_m\text{---}Y]_q$$

wherein PEG is a linear poly(ethylene glycol), alkoxy-poly(ethylene glycol), a branched poly(ethylene glycol), or a forked poly(ethylene glycol) where the PEG has a degree of polymerization of at least about 200, preferably greater than about 1000, and preferably less than about 2000, X is the linking moiety, m is from 1 to about 120, and preferably less than 60, Y is a functional group for attachment to a biologically active agent, and q is equal to the number of polymer end groups and can be from 1 to about 500. Where q is 2, then the Y's can be the same or different, but if q is much greater than 3 or 4, the Y's would normally all be the same group. More generically, in the structure above, PEG can be (Poly)$_a$ and the monomer unit $CH_2CH_2O$ can be represented as (Poly)$_b$ to include similar small polymers, copolymers, oligomers, and the like.

In addition to the above-described forms of PEG, any of the above polymers can also be prepared with one or more weak or degradable linkages in the backbone. For example, PEG can be prepared with ester linkages in the polymer backbone that are subject to hydrolysis. As shown below, this hydrolysis results in cleavage of the polymer into fragments of lower molecular weight:

$$\text{-PEG-CO}_2\text{-PEG-} + H_2O \rightarrow \text{-PEG-CO}_2H + HO\text{-PEG-}$$

Similarly, a polymer backbone can be covalently attached to a biologically active agent through a weak or degradable linkage moiety. For example, ester linkages formed by the reaction of PEG carboxylic acids or activated PEG carboxylic acids with alcohol groups on a biologically active agent generally hydrolyze under physiological conditions to release the agent.

Other hydrolytically degradable linkages, useful as either a degradable linkage within a polymer backbone or as a degradable linkage connecting a polymer backbone to a biologically active agent, include carbonate linkages; imine linkages resulting, for example, from reaction of an amine and an aldehyde (see, e.g., Ouchi et al., Polymer Preprints, 38(1):582–3 (1997), which is incorporated herein by reference.); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

Many other polymers are also suitable for the invention. Polymer backbones that are non-peptidic and water-soluble are particularly useful in the invention. Examples of suitable polymers that may be used in place of PEG in the manner specified above include, but are not limited to, other poly(alkylene glycols), such as poly(propylene glycol) (PPG), copolymers of ethylene glycol and propylene glycol and the like, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof.

Those of ordinary skill in the art will recognize that the foregoing list for substantially water soluble polymers is by no means exhaustive and is merely illustrative, and that all polymeric materials having the qualities described above are contemplated.

Components Forming the X Linking Group

As mentioned, the method and resulting functionalized polymer can be represented by:

$$R\text{-}(Poly)_a\text{-}Z + Y'\text{-}(Poly)_b\text{-}Y \rightarrow Y\text{-}(Poly)_b\text{-}X\text{-}(Poly)_a\text{-}X\text{-}(Poly)_b\text{---}Y$$

Z is a functionalized endgroup of the high weight polymer (Poly)$_a$ and Y and Y' are functionalized endgroups of the low weight polymer (Poly)$_b$. R can include a functionalized end group Z if it is desired to produce a homobifunctional polymer as shown, or a protected active group for later coupling to another activated smaller polymer, activated with a different group Y", if a heterobifunctional large polymer is desired.

Various reactive groups Y, Y', Y" and Z include but are not limited to, N-succinimidyl carbonate (see e.g., U.S. Pat. Nos. 5,281,698, 5,468,478), amine (see, e.g., Buckmann et al. Makromol.Chem. 182:1379 (1981), Zaplipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170–181, Harris & Zaplipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Macrolol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461). All of the above references are incorporated herein by reference.

The endgroups Z and the Y, Y' or Y" groups reactive with Z are selected such that the endgroup moieties are complementary, meaning that the endgroups readily react with one another under reaction conditions to form a linking group X which is typically hydrolytically stable under physiological conditions. It is the formation of the linking group X which binds the high molecular weight polymer to the low molecular weight polymer, thereby forming an overall high molecular weight functionalized polymer derivative. Y, Y', and Y" can be the same or different so long as they are not reactive with each other. Additionally, at least one reactive group Y or Y' should not react with Z so as to provide functionality for the completed polymer.

The functional groups or chemically reactive groups on the low weight polymer may be selected from the group consisting of hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, thiosulfonate, and tresylate.

Reactive endgroups can be selected from one or a combination of the following: —$(CH_2)_r CO_2H$, —$(CH_2)_r CO_2NS$, —$(CH_2)_r CO_2Bt$, —$(CH_2)_r CH(OR)_2$, —$(CH_2)_r CHO$, —$(CH_2)_2$—$NH_2$, —$(CH_2)_r M$, —$(CH_2)_r$—S—$SO_2$—R, where r is 1–5, r' is 0–5, R is aryl or alkyl, NS is N-succinimidyl, Bt is 1-benzotriazolyl, and M is N-maleimidyl.

Typically, the linking moiety X is hydrophilic and short. However, the linking group could be prepared from hydrophobic components so long as, whether hydrophilic or hydrophobic, the linking group does not substantially alter the properties of the polymer. That is, in the case of PEG, the linking group should not alter the properties as set forth above in the definition of PEG.

Reaction Conditions

Suitable solvents providing a medium for the reaction of the Z and Y, Y', or Y" endgroups in formation of the X linking group include but are not limited to toluene, tetrahydrofuran, dioxane, acetonitrile, methylene chloride, chloroform, dimethylformamide, dimethylsulfoxide, benzene, xylenes, and solvents with similar chemical characteristics.

It has been found that the modified and conjugated low weight polymers of the invention may be filtered, separated, and purified with more efficiency and with better results than similarly modified or conjugated high weight polymers of the past. In general, it is easier to separate mixtures of low weight polymers into component species than with similar higher weight polymers.

Endgroup modification and conjugation is generally a multi-step process, with each step of the functionalization resulting in polymeric impurities. If purification is ineffective, which can be the case when dealing with high weight polymers, the impurities accumulate throughout functionalization of the polymer to an unacceptable level. By first performing functionalization and purification processes on a low weight polymer and subsequently joining the purified low weight polymer with a high weight polymer in accordance with this invention, process steps involving the high weight polymer are minimized, resulting in a high weight functionalized or conjugated polymer derivative of overall desirable purity.

Method of Forming the High Molecular Weight Activated Polymer of the Invention

A high molecular weight, water soluble, non-peptidic, polymer having at least one functional group, Z, is covalently attached to a low molecular weight, typically oligomeric, water soluble, non-peptidic, polymer having at least two functional groups, Y' and Y, which may be the same or different, so long as Y is not reactive with Y' and Z is reactive with at least one of Y or Y'. The invention also embodies the conjugation of the polymer derivative with a biologically active agent after the functionalized polymer derivative is produced in accordance with the invention.

In general, the method and resulting functionalized polymer are represented by:

$$(Poly)_a\text{-}Z + Y'\text{-}(Poly)_b\text{-}Y \rightarrow (Poly)_a\text{-}X\text{-}(Poly)_b\text{-}Y$$

where Polya has at least about 200 repeating units, typically at least about 1000, and more typically between 1000 and 2000; and Polyb has from to about 120, and typically less than 60 repeating units. Y and Y' can be the same or different, so long as Y' is not reactive with Y, and are functional groups, and X is a linking molecule formed by the reaction of Z and the Y or Y' components. In the example above Z is reactive with Y' to form a linkage X. $(Poly)_a$ can be additionally functionalized to produce a homobifunctional polymer with Y reactive groups at each terminus. If the additional group is protected from reaction, the protective group can be removed from the resulting polymer conjugate to create a heterobifunctional polymer.

The resulting polymer derivatives of the invention comprise a high molecular weight water soluble polymer segment which is covalently connected, via a linking group, to a low molecular weight water soluble polymer segment. The low molecular weight polymer segment has a functionalized endgroup, Y, in addition to the endgroup which provides the linkage with the high weight polymer segment. The additional functionalized endgroup, Y, upon the low weight polymer segment, provides a linking group for covalently bonding with a biologically active agent or for conversion to such a group.

The following are offered as non-limiting examples of the invention.

EXAMPLE 1

Synthesis of α-t-Boc amino-ω-methanesulfonate PEG(3400)

α-N-t-Boc amino-ω-hydroxy PEG(3400) (MW 3318 Da, 4.0 g, 0.0012 moles) (Shearwater Corp.) was azeotroped in chloroform (80 ml) on a rotary evaporator at 35° C. to dryness and chloroform (50 ml) was added to the residual syrup. The solution was cooled to 4° C. under argon and triethylamine (0.31 ml, 0.0022 moles) was injected, followed by slow injection of methanesulfonyl chloride (0.15 ml, 0.0019 moles). The reaction mixture was stirred overnight under argon while the bath was allowed to rise to ambient temperature. Anhydrous sodium carbonate (4.0 m) was added to the reaction mixture and the resulting solution was stirred at room temperature for one hour. The mixture was then filtered and the filtrate was concentrated to dryness. Isopropanol (40 ml) was added and the precipitated product was collected by filtration and dried under vacuum. Yield 3.7 g α-t-Boc amino-ω-methanesulfonate PEG(3400). NMR (DMSO-d6): 1.37 ppm (s, —OC(CH$_3$)$_3$), 3,51 ppm (s, PEG backbone), 4.31 ppm (t, —CH$_2$SO$_2$—), 6.76 ppm (—CH$_2$NH—CO—). This example demonstrates how the functional group, Y, of the low weight polymer, α-N-t-Boc amino-ω-hydroxy PEG(3400), is modified with a good yield of modified low weight polymer.

EXAMPLE 2

Synthesis of α-t-Boc amino-ω-p-toluenethiosulfonate PEG(3400)

α-t-Boc amino-ω-methanesulfonate PEG(3400) (the product of Ex. 1)(1.0 g, 0.30 mmoles) was azeotroped to dryness in chloroform (30 ml) on a rotary evaporator at 35° C. and anhydrous ethanol (15 ml) was added to the residual syrup. Potassium p-toluenethiosulfonate (292 mg, 1.25 mmoles) was added and the mixture was refluxed under argon overnight. The solvent was removed on a rotary evaporator at 40° C. and the residue was dried under vacuum for 30 minutes. The crude product was dissolved in 100 ml 1M $NaH_2PO_4$—$Na_2HPO_4$ buffer solution (contain 10 wt % NaCl) at pH 5.8. and the resulting solution was extracted with dichloromethane (100 ml×3). The dichloromethane phase was dried over anhydrous sodium sulfate, filtered, and the filtrate concentrated to near dryness on a rotary evaporator. The product was precipitated by addition of isopropanol/ether (40 ml/20 ml), collected by filtration, and dried under vacuum. Yield: 0.7 α-t-Boc amino-ω-p-toluenethiosulfonate PEG(3400). NMR: (DMSO-d6): 1.37 ppm (s, —$OC(CH_3)_3$), 2.43 ppm (s, $CH_3$—$CH_2$=$CH_2$/Ar), 3,51 ppm (s, PEG backbone), 6.76 ppm (t, —$CH_2NH$—CO—), 7.49 ppm (dd, $CH_3$—$CH_2$=$CH_2$/Ar), 7.82 ppm (dd, $CH_3$—$CH_2$=$CH_2$/Ar). This example again demonstrates how the functional group, Y, of the low weight polymer, α-t-Boc amino-ω-methanesulfonate PEG(3400), is modified with a good yield of modified low weight polymer.

EXAMPLE 3

Synthesis of α-$NH_2$-ω-p-toluenethiosulfonate PEG (3400)

α-t-Boc amino-ω-p-toluenethiosulfonate PEG(3400) (the product of Ex. 2) (0.7 g) was dissolved in anhydrous dichloromethane (3.5 ml). and trifluroacetic acid (3.5 ml) under argon. The solution was stirred at room temperature for one hour and concentrated to dryness. Isopropanol (20 mL) was added and the precipitated product was collected by filtration and dried under vacuum. Yield: 0.6 g α-$NH_2$-ω-p-toluenethiosulfonate PEG(3400). NMR (DMSO-d6): 2.43 ppm (s, $CH_3$—$CH_2$=$CH_2$/Ar), 2.95 ppm (t, —$OCH_2CH_2NH_2$), 3,51 ppm (s, PEG backbone), 7.49 ppm (dd, $CH_3$—$CH_2$=$CH_2$/Ar), 7.82 ppm (dd, $CH_3$—$CH_2$=$CH_2$/Ar). This example again demonstrates how the functional group, Y, of the low weight polymer, α-t-Boc amino-ω-p-toluenethiosulfonate PEG(3400), is modified with a good yield of modified low weight polymer.

EXAMPLE 4

Synthesis of mPEG(23.4 kDa)-p-toluenethiosulfonate

MPEG(20 kDa)-1-benzotriazole (813 mg, MW 21 kDa, 0.039 mmoles) (Shearwater Corp.) and PEG(3400)-α-$NH_2$-ω-p-toluenethiosulfonate (the product of Ex. 3) (MW 3805 Da, 200 mg, 0.053 mmoles) were dissolved in anhydrous dichloromethane (20 ml) under argon and triethylamine (30.8 μl, 0.22 mmoles) was injected. The solution was stirred at room temperature overnight, then concentrated to dryness. 2-Propanol (10 ml) was added and the precipitated product was collected by filtration and dried under vacuum. Yield: 843 mg. The crude mPEG (23.4 kDa)-p-toluenethiosulfonate (560 mg) in 50 mL de-ionized water. was loaded onto a column packed with 50 ml Poros media. The column was eluted with 100 ml de-ionized water. Sodium chloride (15) was added to the eluant and the resulting solution was extracted with dichloromethane (100 ml×3). The extract was dried over anhydrous sodium sulfate, filtered, and the filtrate concentrated to near dryness on a rotary evaporator. Ethyl ether (50 ml) was added to precipitate the product. The product was collected by filtration and dried under vacuum. Yield 495 mg mPEG(23.4 kDa)-p-toluenethiosulfonate. NMR (DMSO-d6): 2.43 ppm (s, $CH_3$—$CH_2$=$CH_2$/Ar), 3,51 ppm (s, PEG backbone), 7.23 ppm (t, —NHCOO—), 7.49 ppm (dd, $CH_3$—$CH_2$=$CH_2$/Ar), 7.82 ppm (dd, $CH_3$—$CH_2$=$CH_2$/Ar). This example demonstrates the combination of a high weight polymer, MPEG(20 kDa)-1-benzotriazole, with a modified low weight polymer, PEG(3400)-α-$NH_2$-ω-p-toluenethiosulfonate, by reaction of the Z functional group, benzotriazole, with the Y' functional group, amine, to form a linking group between the high weight and low weight polymer segments.

EXAMPLE 5

PEGylation of α1-antitrypsin

To a solution of α1-antitrypsin (1 mg, Sigma, MW 25 kDa) in 100 mM sodium phosphate (pH 7.2, 1 ml) was added 2.8 mg of mPEG p-toluenethiolsulfonate (the product of Ex. 4) (24 kDa) and the solution was stirred overnight at room temperature. Capillary electrophoresis indicated that the PEG α1-antitrypsin conjugate was formed in 36% yield. SDS gel electrophoresis also demonstrated the presence of the PEG conjugate. Treatment of the PEG conjugate with β-mercaptoethanol resulted in the formation of α1-antitrypsin as evidenced by gel electrophoresis, thus indicating the presence of a disulfide linkage in the PEG α1-antitrypsin conjugate. This example demonstrates the combination of a biologically active agent, α1-antitrypsin, with the high weight polymer derivative of Ex. 4 via the functionalized endgroup Y, p-toluenethiolsulfonate.

EXAMPLE 6 m-PEG(22 KDa)-propionic acid

To a solution of m-PEG(20 KDa)-benzotriazole carbonate (2.0 g, 0.0001 moles) (Shearwater Corporation) in methylene chloride (20 ml), PEG(2 KDa)-α-amino-oω-propionic acid (0.24 g, 0.00012 moles) (Shearwater Corporation) and triethylamine (0.060 ml) were added and the reaction mixture was stirred overnight at room temperature under argon atmosphere. Next the mixture was filtered and solvent was evaporated to dryness. The crude product was dissolved in methylene chloride and precipitated with isopropyl alcohol. The wet product was dried under reduced pressure. Yield 1.9 g. NMR ($d_6$-DMSO): 2.44 ppm (t, —$CH_2$—COO—), 3.11 ppm (q, —$\underline{CH_2}$—NH—), 3.24 ppm (s, —$OCH_3$), 3.51 ppm (s, PEG backbone), 4.04 ppm (m, —$CH_2$—O(C=O)—), 7.11 ppm (t, —(C=O)—NH—). Anion exchange chromatography yielded m-PEG(22 KDa)-propionic Acid (93%) and m-PEG-20KDa (7%). This example demonstrates the combination of a high weight polymer, m-PEG(20 KDa)-benzotriazole carbonate, with a low weight polymer, PEG(2 KDa)-α-amino-ω-propionic acid, via the functionalized carbonate, Z, and amino, Y', endgroups.

EXAMPLE 7 m-PEG(22 KDa)-propionic acid, N-hydroxysuccinimide ester

To a solution of m-PEG(22 KDa)-propionic acid (the product of Ex. 6) (1.1 g, 0.000050 moles) in anhydrous methylene chloride (10 ml), N-hydroxysuccinimide (0.0063 g, 0.000055 moles) was added followed by 1,3-dicyclohexylcarbodiimide (1.0 M solution in methylene chloride, 0.05 ml, 0.000055 moles). The reaction mixture was stirred overnight at room temperature under argon. Next the mixture was filtered and the solvent was evaporated. The crude product was dissolved in methylene chloride, precipitated with isopropyl alcohol, and dried under reduced pressure. Yield 0.9 g. NMR ($d_6$-DMSO): 2.81 ppm (s, —$CH_2$—

$CH_2$— (succinate)), 2.92 ppm (t, —$CH_2$—COO—), 3.11 ppm (q, —$\underline{CH_2}$—NH—), 3.24 ppm (s, —$OCH_3$), 3.51 ppm (s, PEG backbone), 4.03 ppm (m, —$CH_2$—O(C=O)—), 7.11 ppm (t, —(C=O)—NH—). This example demonstrates the modification of the functional group, Y, of the polymer produced in Ex. 6 from propionic acid to propionic acid, N-hydroxysuccinimide ester.

EXAMPLE 8

PEG(2 KDa)-α-amino-ω-propionic acid, methyl ester

To a solution of PEG(2 KDa)-α-amino-ω-propionic acid (10 g, 0.0050 moles) (Shearwater Corporation) in anhydrous methylene chloride (100 ml) 1-hydroxybenzotriazole (0.30), 4-(dimethylamino)pyridine (1.0), methyl alcohol (3.2 g, 0.100 moles) and 1,3-dicyclohexylcarbodiimide (1.0 M solution in methylene chloride, 7.5 ml, 0.0075 moles) were added. The reaction mixture was stirred overnight at room temperature under argon. Next the mixture was concentrated to about 50 ml, filtered and added to 800 ml of cold diethyl ether. The precipitated product was filtered off and dried under reduced pressure. Yield 9.5 g. NMR ($d_6$-DMSO): 2.53 ppm (t, —$CH_2$ —COO—), 2.95 ppm (t, —$CH_2$—amine), 3.51 ppm (s, PEG backbone). This example demonstrate the modification of the functional endgroup, Y, of the low weight polymer, PEG(2 KDa)-α-amino-ω-propionic acid, from propionic acid to propionic acid, methyl ester.

EXAMPLE 9 m-PEG(32 KDa)-propionic acid, methyl ester

To a solution of m-PEG(30 KDa)-benzotriazole carbonate (3.0 g, 0.0001 moles) (Shearwater Corporation) in methylene chloride (20 ml), PEG(2 KDa)-α-amino-ω-propionic acid, methyl ester (the product of Ex. 8) (0.24 g, 0.00012 moles) and triethylamine (0.060 ml) were added and the reaction mixture was stirred overnight at room temperature under argon. Next the mixture was filtered and the solvent was evaporated. The crude product was dissolved in methylene chloride, precipitated with isopropyl alcohol, and dried under reduced pressure. Yield 2.8. NMR ($d_6$-DMSO): 2.53 ppm (t, —$CH_2$—COO—), 3.11 ppm (q, —$\underline{CH_2}$—NH—), 3.24 ppm (s, —$OCH_3$), 3.51 ppm (s, PEG backbone), 4.04 ppm (m, —$CH_2$—O(C=O)—), 7.11 ppm (t, —(C=O)—NH—). This example demonstrates the combination of the low weight polymer produced in Ex. 8 with the high weight polymer, m-PEG(30 KDa)-benzotriazole carbonate, via the Z, benzotriazole carbonate, and Y', amino, functional groups.

EXAMPLE 10 m-PEG(32 KDa)-propionic acid m-PEG(32 KDa)-propionic acid, methyl ester (the product of Ex. 9) (2.8 g, 0.000082 moles) was dissolved in 20 ml deionized water and the pH was adjusted to 12.0 with 0.5 M NaOH solution. The reaction mixture was stirred 1.5 h at pH=12.0+/−0.1. Next sodium chloride (3 g) was added and the pH was adjusted to 3 with 5-% phosphoric acid. The product was extracted with methylene chloride 3 times and the combined extracts were dried with anhydrous magnesium chloride. The solvent was removed under reduced pressure and the product dried under reduced pressure. Yield 1.6. NMR ($d_6$-DMSO): 2.44 ppm (t, —$CH_2$ —COO—), 3.11 ppm (q, —$\underline{CH_2}$—NH—), 3.24 ppm (s, —$OCH_3$), 3.51 ppm (s, PEG backbone), 4.04 ppm (m, —$CH_2$—O(C=O)—), 7.11 ppm (t, —(C=O)—NH—). Anion exchange chromatography gave m-PEG(32KDa)-propionic Acid (97.5%), M-PEG-30 KDa (2.5%). This example demonstrates the modification of the functional group, Y, of the polymer produced in Ex. 9, from propionic acid, methyl ester to propionic acid.

EXAMPLE 11 m-PEG(32 KDa)-propionic acid, N-hydroxysuccinimide ester

To a solution of m-PEG(32 KDa)-propionic acid (product of Ex. 10) (1.6 g, 0.000050 moles) in anhydrous methylene chloride (10 ml), N-hydroxysuccinimide (0.0063 g, 0.000055 moles) was added followed by 1,3-dicyclohexylcarbodiimide (1.0 M solution in methylene chloride, 0.05 ml, 0.000055 moles). The reaction mixture was stirred overnight at room temperature under argon, filtered and the solvent was evaporated. The crude product was dissolved in methylene chloride, precipitated with isopropyl alcohol, and dried under reduced pressure. Yield 0.9 g. NMR ($d_6$-DMSO): 2.81 ppm (s, —$CH_2$—$CH_2$— (succinate)), 2.92 ppm (t, —$CH_2$—COO—), 3.11 ppm (q, —$\underline{CH_2}$—NH—), 3.24 ppm (s, —$OCH_3$), 3.51 ppm (s, PEG backbone), 4.03 ppm (m, —$CH_2$—O(C=O)—), 7.11 ppm (t, —(C=O)—NH—). This example demonstrates the modification of the functional group, Y, of the polymer produced in Ex. 9 from propionic acid to propionic acid, N-hydroxysuccinimide ester.

EXAMPLE 12 m-PEG(23.4 KDa)-butanoic acid

To a solution of m-PEG(20 KDa)-benzotriazole carbonate (2.0 g, 0.0001 moles) (Shearwater Corporation) in methylene chloride (20 ml), PEG(3.4 KDa)α-amino-ω-butanoic acid (0.45 g, 0.00012 moles) (Shearwater Corporation) and triethylamine (0.060 ml) were added and the reaction mixture was stirred overnight at room temperature under argon atmosphere. Next the mixture was filtered and solvent was evaporated to dryness. The crude product was dissolved in methylene chloride, precipitated with isopropyl alcohol, and the product dried under reduced pressure. Yield 2.2 g. NMR ($d_6$-DMSO): 1.72 ppm (q, $\underline{CH_2}$—$CH_2$—COO—) 2.24 ppm (t, —$CH_2$—COO—), 3.11 ppm (q, —$\underline{CH_2}$—NH—), 3.24 ppm (s, —$OCH_3$), 3.51 ppm (s, PEG backbone), 4.04 ppm (m, —$CH_2$—O(C=O)—), 7.11 ppm (t, —(C=O)—NH—). Anion exchange chromatography yielded m-PEG(23.4 KDa)-butanoic acid (92%), M-PEG-20 KDa (8%). This example demonstrates the combination of the low weight polymer, PEG(3.4 KDa)-α-amino-ω-butanoic acid, with the high weight polymer, m-PEG(20 KDa)-benzotriazole carbonate, via the benzotriazole carbonate, Z, and amino, Y', functional groups.

EXAMPLE 13 m-PEG(22 KDa)-butanoic acid, N-hydroxysuccinimide ester

To a solution of m-PEG(23.4 KDa)-butanoic acid (product of Ex. 12) (1.17 g, 0.000050 moles) in anhydrous methylene chloride (10 ml), N-hydroxysuccinimide (0.0063 g, 0.000055 moles) was added followed by 1,3-dicyclohexylcarbodiimide (1.0 M solution in methylene chloride, 0.05 ml, 0.000055 moles). The reaction mixture was stirred overnight at room temperature under argon, filtered and solvent was evaporated to dryness. The crude product was dissolved in methylene chloride, precipitated with isopropyl alcohol, and dried under reduced pressure. Yield 1.0 g. NMR (d$_6$-DMSO): 1.83 ppm (q, CH$_2$—CH$_2$—COO—), 2.70 ppm (t, —CH$_2$—COO—), 2.81 ppm (s, —CH$_2$—CH$_2$— (succinate)), 2.92 ppm, 3.11 ppm (q, —CH$_2$—NH—), 3.24 ppm (s, —OCH$_3$), 3.51 ppm (s, PEG backbone), 4.03 ppm (m, —CH$_2$—O(C=O)—), 7.11 ppm (t, —(C=O)—NH—). This example demonstrates the modification of the functional group, Y, of the polymer produced in Ex. 12, from butanoic acid to butanoic acid, N-hydroxysuccinimide ester.

EXAMPLE 14 m-PEG(20 KDa)-amine

To a solution of m-PEG(20 KDa)-benzotriazole carbonate (2.0 g, 0.0001 moles) (Shearwater Corporation) in methylene chloride (20 ml), triethylene glycol diamine FW=148.21 (0.3 g, 0.0020 moles) was added and the reaction mixture was stirred 2 h at room temperature under argon. Next the solvent was evaporated to dryness and the crude product dissolved in methylene chloride and precipitated with isopropyl alcohol. The product was dried under reduced pressure. Yield 1.8 g. NMR (d$_6$-DMSO): 2.64 ppm (t, —CH$_2$-amine-), 3.11 ppm (q, —CH$_2$—NH—), 3.24 ppm (s, —OCH$_3$), 3.51 ppm (s, PEG backbone), 4.04 ppm (m, —CH$_2$—O(C=O)—), 7.11 ppm (t, —(C=O)—NH—). Cation exchange chromatography yielded m-PEG(20K)-amine (97.5%). This example demonstrates the combination of the low weight polymer, triethylene glycol diamine, with the high weight polymer, m-PEG(20 KDa)-benzotriazole carbonate, via the benzotriazole carbonate, Z, and amino, Y', functional groups.

EXAMPLE 15

PEG(3.4 KDa)-α-amine-ω-propionaldehyde, diethyl acetal

To a solution of PEG(3.4 KDa)-α-hydroxy-ω-propionaldehyde, diethyl acetal (NOF) (1.0 g, 0.000294 moles) in a mixture of toluene (20 ml) and dichloromethane (5 ml), triethylamine (0.07 ml, 0.000502 moles, 171% of stoichiometric amount) and methanesulfonyl chloride (0.028 ml, 0.000362 moles, 123% of stoichiometric amount) were added and the resulting mixture was stirred overnight under nitrogen atmosphere. The mixture was filtered and solvent was distilled off under reduced pressure. The residue was added to the mixture of 16 ml concentrated ammonium hydroxide and 1.6 ammonium chloride and stirred 42 hours at room temperature. The reaction product was extracted with dichloromethane (3 times 20 ml). The extract was washed with 5 ml 1 M hydrochloric acid, 5 ml distilled water and dried with anhydrous sodium sulfate. Next the solvent was distilled under reduced pressure giving 0.78 g of PEG (3.4 KDa)-α-amine hydrochloride-ω-propionaldehyde, diethyl acetal. NMR (d$_6$-DMSO): 1.10 ppm (t, CH$_3$—, acetal), 1.74 ppm (q, —OCH$_2$CH$_2$CH—, acetal), 2.94 ppm (t, —CH$_2$-amine hydrochloride), 3.51 ppm (s, PEG backbone), 4.55 ppm (t, —CH—, acetal), 7.11 ppm (t, —(C=O)—NH—). This example demonstrates the modification of the functional endgroup, Y', of the low weight polymer, PEG(3.4 KDa)-α-hydroxy-ω-propionaldehyde, from a hydroxy to an amine group.

EXAMPLE 16 m-PEG(23.4 KDa)-propionaldehyde, diethyl acetal

To a solution of m-PEG(20 KDa)-benzotriazole carbonate (2.0 g, 0.0001 moles) (Shearwater Corporation) in methylene chloride (20 ml), PEG(3.4 KDa)-α-amine-ω-propionaldehyde diethyl acetal (0.36 g, 0.000106 moles) was added and the reaction mixture was stirred overnight at room temperature under argon atmosphere. Next the solvent was evaporated to dryness. The crude product was dissolved in methylene chloride and precipitated with isopropyl alcohol. The wet product was dried under reduced pressure. Yield 1.8 g. NMR (d$_6$-DMSO): 1.10 ppm (t, CH$_3$—, acetal), 1.74 ppm (q, —OCH$_2$CH$_2$CH—, acetal), 3.11 ppm (q, —CH$_2$—NH—), 3.24 ppm (s, —OCH$_3$), 3.51 ppm (s, PEG backbone), 4.04 ppm (m, —CH$_2$—O(C=O)—), 4.55 ppm (t, —CH—, acetal), 7.11 ppm (t, —(C=O)—NH—). This example demonstrates the combination of the low weight polymer produced in Ex. 15 PEG(3.4 KDa)-α-amine-ω-propionaldehyde diethyl acetal, with the high weight polymer, m-PEG(20 KDa)-benzotriazole carbonate, via the benzotriazole carbonate, Z, and amino, Y', functional groups.

EXAMPLE 17 m-PEG(23.4 KDa)-propionaldehyde m-PEG(23.4 KDa)-propionaldehyde, diethyl acetal (product of Ex. 16) (1.8) was dissolved in 20 ml water and the pH of the solution was adjusted to 3 with dilute phosphoric acid. The solution was stirred 3 hours at room temperature and 0.5M sodium hydroxide was used to adjust the pH of the solution to 7. The product was extracted with methylene chloride, the extract dried with anhydrous magnesium sulfate, and solvent distilled off under reduced pressure. Yield: 1.6 g. NMR (d$_6$-DMSO): 2.60 ppm (dt, —OCH$_2$CH$_2$CH—, aldehyde), 3.24 ppm (q, —CH$_2$—NH—), 3.51 ppm (s, PEG backbone), 4.04 ppm (m, —CH$_2$—O(C=O)—), 7.11 ppm (t, —(C=O)—NH—), 9.65 ppm (t, —CH, aldehyde). This example demonstrates the modification of the functional group, Y, of the polymer produced in Ex. 16 from propionaldehyde, diethyl acetal to propionaldehyde.

EXAMPLE 18

Branched PEG2(43.4 KDa)-propionaldehyde, diethyl acetal

To a solution of branched PEG2 (40 KDa)-N-hydroxysuccinimide ester (1.0 g, 0.000025 moles) (Shearwater Corporation) in methylene chloride (8 ml), PEG(3.4 KDa)-α-amine hydrochloride-ω-propionaldehyde diethyl acetal (0.12 g, 0.0000352 moles) and triethylamine (0.01 ml) were added and the reaction mixture was stirred overnight at room temperature under argon atmosphere. Next the solvent was evaporated to dryness. The crude product was dissolved in methylene chloride and precipitated with diethyl ether. The wet product was dried under reduced pressure. Yield 0.83 g. NMR (d$_6$-DMSO): 1.10 ppm (t, CH$_3$—, acetal), 1.74 ppm (q, —OCH$_2$CH$_2$CH—, acetal), 3.24 ppm (s, —OCH$_3$), 3.51 ppm (s, PEG backbone), 4.55 ppm (t, —CH—, acetal). This example demonstrates the combination of the low weight polymer, PEG(3.4 KDa)-α-amine hydrochloride-ω-propionaldehyde diethyl acetal, with the high weight branched polymer, PEG2 (40 KDa)-N-hydroxysuccinimide ester, via the N-hydroxysuccinimide ester, Z, and amine hydrochloride, Y', functional groups.

EXAMPLE 19

Branched PEG2(43.4 KDa)-propionaldehyde

Branched PEG2(43.4 KDa)-propionaldehyde, diethyl acetal (product of Ex. 18) (0.4) was dissolved in 10 ml water and the pH of the solution was adjusted to 3 with diluted phosphoric acid. The solution was stirred 3 hours at room temperature and 0.5M sodium hydroxide was used to adjust the pH of the solution to 7. The product was extracted with methylene chloride. The extract was dried with anhydrous magnesium sulfate and solvent was distilled off under reduced pressure. Yield 0.35 g. NMR ($d_6$-DMSO): 2.60 ppm (dt, —OCH$_2$CH$_2$CH—, aldehyde), 3.24 ppm (s, —OCH$_3$), 3.51 ppm (s, PEG backbone), 9.65 ppm (t, —CH, aldehyde). This example demonstrates the modification of the endgroup, Y, of the polymer produced in Ex. 18 from propionaldehyde, diethyl acetal to propionaldehyde.

EXAMPLE 20

M-PEG$_{20k}$-Maleimide

To a solution of m-PEG(20 KDa)-benzotriazole carbonate (20.0 g, 0.001 moles) (Shearwater Corporation) in methylene chloride (200 ml), Maleimide-triethyleneglycol-amine TFA (0.68 g, 0.002 moles) and 4-methylmorpholine (0.44 ml, 0.004 moles) were added. The reaction was stirred 4 hours at room temperature under argon. Next the solvent was evaporated to dryness and precipitated with isopropyl alcohol (1000 ml). The precipitate was collected by vacuum filtration and dried in vacuo overnight. Yield: 19.5 g. NMR (d6-DMSO): 3.11 ppm(q, —CH$_2$—NH—), 3.24 ppm (s, —OCH$_3$), 3.51 ppm (s, PEG backbone), 4.04 ppm (t,— CH$_2$—O(C=O)—), 7.04 ( s, —(C=O)—CH=CH—(C=O)—), 7.11 ppm ( t, —(C=O)—NH—). This example demonstrates the combination of the high weight polymer, m-PEG(20 KDa)-benzotriazole carbonate, with the low weight polymer, Maleimide-triethyleneglycol-amine TFA, via the benzotriazole carbonate, Z, and amine, Y', functional groups.

What is claimed is:

1. An activated polymer derivative, said polymer derivative comprising one or more first water soluble, non-peptidic polymeric segments having at least about 200 repeating units covalently attached through at least one linkage moiety to at least one second water soluble, non-peptidic polymeric segment having no more than about 120 repeating units, wherein said units of said first and second polymeric segments may be the same or different, wherein said at least one linkage moiety does not substantially alter the properties of said polymer derivative, said polymeric derivative having at least one active moiety selected from the group consisting of electrophilic moieties and nucleophilic moieties located on one of said first and second polymeric segments.

2. The polymer derivative of claim 1, wherein said at least one active moiety is a single moiety located on said second polymeric segment.

3. The polymer derivative of claim 1, wherein said first polymer segment further comprises a protected functional group.

4. The polymer derivative of claim 1, wherein the first and second polymeric segments are independently selected from the group consisting of poly(alkylene glycol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), and copolymers, terpolymers, and mixtures thereof.

5. The polymer derivative of claim 1, wherein said first polymeric segment has from about 200 to 2000 repeat monomer units.

6. The polymer derivative of claim 4, wherein said first polymeric segment has from about 200 to 700 repeating units.

7. The polymer derivative of claim 1, wherein said second polymeric segment has from 1 to about 120 repeating units.

8. The polymer derivative of claim 1, wherein said second polymeric segment has from about 40 to 80 repeating units.

9. The polymer derivative of claim 1, wherein said first and second polymeric segments are poly(ethylene glycol).

10. The polymer derivative of claim 1, wherein said linkage moiety between said first and second polymeric segments is a hydrophilic moiety selected from an amide or carbamate linkage.

11. The polymer derivative of claim 1, wherein said active moiety is selected from the group consisting of hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, malcimide, vinylsulfone, dithiopyridine, vinylpyridine, indoacetamide, epoxide, glyoxals, diones, mesylates, tosylates, thiosulfonate, and tresylate.

12. The polymer derivative of claim 1, wherein said polymeric segments are selected from the group consisting of linear, branched, and multiarmed polymeric segments.

13. An activated polymer derivative, said polymer derivative comprising a linear monomethoxy poly(ethylene glycol) segment having from about 200 to 700 repeating monomer units covalently attached through at least one amide or carbamate linkage moiety to one terminus of a linear poly(ethylene glycol) segment having from 1 to 120 repeating monomer units, and wherein said poly(ethylene glycol) segment of 1 to 120 repeating monomer units includes at least one active moiety selected from the group consisting of electrophilic moieties and nucleophilic moieties at the terminus thereof opposite said poly(ethylene glycol) segment of 200 to 700 repeating monomer units.

14. A polymer derivative selected from the group consisting of monomethoxy poly(ethylene glycol)-p-toluenethiosulfonate; monomethoxy poly(ethylene glycol)-propionic acid; monomethoxy poly(ethylene glycol)-propionic acid, N-hydroxysuccinimide ester; monomethoxy poly(ethylene glycol)-propionic acid, methyl ester; monomethoxy poly(ethylene glycol)-butanoic acid; monomethoxy poly(ethylene glycol)-butanoic acid, N-hydroxysuccinimide ester; monomethoxy poly(ethylene glycol)-butanoic acid, methyl ester; monomethoxy poly (ethylene glycol)-amine; monomethoxy poly(ethylene glycol)-propionaldehyde; monomethoxy poly(ethylene glycol)-propionaldehyde, diethyl acetal; di-monomethoxy poly(ethylene glycol)-lysine propionaldehyde; di-monomethoxy poly(ethylene glycol)-lysine propionaldehyde, diethyl ester; and monomethoxy poly (ethylene glycol)-malemide; wherein said polymer derivative has a molecular weight of at least about 10,000 Daltons and has at least two distinct poly(ethylene glycol) segments attached by a linking group.

15. The polymer derivative of claim 14 conjugated to a biologically active molecule.

16. The polymer derivative of claim 1, having the structure (Poly)$_a$-X-(Poly)$_b$-Y, wherein (Poly)$_a$ is a water-soluble, non-peptidic polymeric segment having more than about 200 repeating units, X is a linking moiety that does not substantially alter the properties of the polymer derivative, (Poly)$_b$ is a water-soluble, non-peptidic polymeric segment having from 1 to about 120 repeating units, which may the same as or different from (Poly)$_a$, and Y is an electrophilic or nucleophilic moiety.

17. The polymer derivative of claim 1, having the structure Y-(Poly)$_b$-X-(Poly)$_a$-X-(Poly)$_b$-Y-, wherein (Poly)$_a$ is a water-soluble, non-peptidic polymeric segment having more than about 200 repeating units, X is a linking moiety that does not substantially alter the properties of the polymer derivative, (Poly)$_b$ is a water-soluble, non-peptidic polymeric segment having from 1 to about 120 repeating units, and wherein Y is an electrophilic or nucleophilic moiety.

18. The polymer of claim 1, wherein said active moiety is selected from the group consisting of —$(CH_2)_rCO_2H$, —$(CH_2)_rCO_2NS$, —$(CH_2)_rCO_2Bt$, —$(CH_2)_rCH(OR)_2$, —$(CH_2)_rCHO$, —$(CH_2)_2$—$NH_2$, —$(CH_2)_rM$, and —$(CH_2)_r$—S—$SO_2R$, wherein r is 1–5 r' is 0–5, R is aryl or alkyl, NS is N-succinimidyl, Bt is 1-benzotriazolyl, and M is N-maleimidyl.

19. The polymer of claim 1, wherein one or both of said first and second polymeric segments further comprise groups that degrade hydrolytically or enzymatically between said monomers.

20. A polymer having the composition PEG-[X—$(CH_2CH_2O)_m$—Y]$_q$ wherein:
   PEG is a water-soluble non-peptidic polymer selected from the group consisting of a linear poly(ethylene glycol), alkoxy-poly(ethylene glycol), a branched poly(ethylene glycol), and a forked poly(ethylene glycol), with or without hydrolytically or enzymatically degradable linkages, where the poly(ethylene glycol) has at least 200 repeating monomer units,
   X is a linking moiety,
   m is from 1 to about 120,
   Y is a moiety having a terminal electrophilic or nucleophilic group, and
   q is from 1 to about 500.

21. The polymer of claim 20, wherein Y is selected from the group consisting of hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, thiosulfonate, and tresylate.

22. The polymer of claim 20, wherein for q=2, Y is independently selected from the group consisting of hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, thiosulfonate, and tresylate.

23. The polymer of claim 20, wherein Y is selected from the group consisting of —$(CH_2)_rCO_2H$, —$(CH_2)_rCO_2NS$, —$(CH_2)_{r'}$—$CO_2Bt$, —$(CH_2)_rCH(OR)_2$, —$(CH_2)_rCHO$, —$(CH_2)_2$—$NH_2$, —$(CH_2)_rM$, and —$(CH_2)_r$—S—$SO_2$—R, where r is 1–5, r' is 0–5, R is aryl or alkyl, NS is N-succinimidyl, Bt is 1-benzotriazolyl, and M is N-maleimidyl.

24. The polymer of claim 20, wherein X is an amide or carbamate linkage.

25. The polymer of claim 20, where the poly(ethylene glycol) has from about 200 to 2000 repeating units.

26. A polymer having the composition R—$(OCH_2CH_2)_n$—X—$(CH_2CH_2$—$O)_m$—Y
where:
   R is selected from an alkyl group having from 1 to 5 carbon atoms and a functional moiety having a terminal electrophilic or nucleophilic group,
   n is greater than 200,
   m is between 1 and about 120,
   X is a linking moiety, and
   Y is a moiety having a terminal electrophilic or nucleophilic group, which may be the same or different from R.

27. A method of forming a water-soluble, non-peptidic polymer with at least one functional group, said method comprising the steps of:
   providing a first water soluble, non-peptidic polymer composed of at least about 200 repeating units and having at least one first functional group;
   providing a second water soluble, non-peptidic polymer composed of from 1 to about 120 repeating units and having at least one of a second functional group, said second functional group being reactive with said first functional group of the high weight polymer, at least; and wherein at least one of said first and second polymers further comprises a functional group that is not reactive with either of said first and second functional groups,
   reacting said first and second functional groups, thereby covalently bonding said first and second polymers to provide a water-soluble, non-peptidic polymer with at least one functional group.

28. The method of claim 27, wherein the first and second functional groups are selected from the group consisting of N-succinimidyl carbonate, amino, hydrazide, succinimidyl propionate and succinimidyl butanoate, succinimidyl succinate, succinimidyl ester, benzotriazole carbonate, glycidyl ether, oxycarbonylimidazole, p-nitrophenyl carbonate, aldehyde, maleimide, orthopyridyl-disulfide, acrylol, and vinylsulfone.

29. The method of claim 27, wherein the functional group that is not reactive with the first and second functional groups is selected from the group consisting of hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, thiosulfonate, and tresylate.

30. The method of claim 27, wherein the first and second functional groups are reacted in the presence of a solvent selected from the group consisting of toluene, tetrahydrofuran, dioxane, acetonitrile, methylene chloride, chloroform, dimethylformamide, dimethylsulfoxide, benzene, xylene, and combinations thereof.

31. The method of claim 27, wherein the polymers are each poly(ethylene glycol) selected from the group consisting of monofunctional and difunctional linear, branched, multiarmed, and forked forms.

32. The method of claim 27, wherein the first polymer is a linear methoxy-poly(ethylene glycol).

33. The method of claim 27, further comprising the step of conjugating the functional group that is not reactive to the first and second functional groups to a biologically active agent.

34. The method of claim 33, wherein the biologically active agent is selected from the group consisting of protein, peptide, carbohydrate, oligonucleotide, DNA, RNA, and lipid.

35. The method of claim 27, wherein the first polymer comprises a protected reactive group and further including the step of removing the protecting moiety from the covalently bonded high and low weight polymers to create an additional functionality.

36. The polymer derivative of claim 1 conjugated to a biologically active molecule.

37. The polymer derivative of claim 36, wherein the biologically active molecule is selected from the group consisting of protein, peptide, carbohydrate, oligonucleotide, DNA, RNA, and lipid.

38. The polymer derivative of claim 13 conjugated to a biologically active molecule.

39. The polymer derivative of claim 38, wherein the biologically active molecule is selected from the group consisting of protein, peptide, carbohydrate, oligonucleotide, DNA, RNA, and lipid.

40. The polymer of claim 20 conjugated to a biologically active molecule.

41. The polymer of claim 40, wherein the biologically active molecule is selected from the group consisting of protein, peptide, carbohydrate, oligonucleotide, DNA, RNA, and lipid.

42. The polymer of claim 26 conjugated to a biologically active molecule.

43. The polymer of claim 42, wherein the biologically active molecule is selected from the group consisting of protein, peptide, carbohydrate, oligonucleotide, DNA, RNA, and lipid.

44. The polymer derivative of claim 15, wherein the biologically active molecule is selected from the group consisting of protein, peptide, carbohydrate, oligonucleotide, DNA, RNA, and lipid.

45. The polymer derivative of claim 14, wherein said polymer derivative comprises a first poly(ethylene glycol) segment having at least about 200 repeating units covalently attached through a linkage moiety to a second poly(ethylene glycol) segment having no more than about 120 repeating units, and wherein said linkage moiety does not substantially alter the properties of said polymer derivative.

* * * * *

UNITED STATES PATENT AND TRADEMARK OFFICE
CERTIFICATE OF CORRECTION

PATENT NO. : 6,774,180 B2
DATED : August 10, 2004
INVENTOR(S) : Kozlowski et al.

It is certified that error appears in the above-identified patent and that said Letters Patent is hereby corrected as shown below:

Column 20,
Line 17, "malcimide" should read -- maleimide --;
Line 18, "indoacetamide" should read -- iodoacetamide --;

Column 22,
Line 29, "amino" should read -- amine --.

Signed and Sealed this

Eighth Day of February, 2005

JON W. DUDAS
*Director of the United States Patent and Trademark Office*